[19] United States Patent
Fruchey et al.

[11] Patent Number: 5,981,799
[45] Date of Patent: Nov. 9, 1999

[54] METHOD FOR THE PURIFICATION OF ACETAMINOPHEN

[75] Inventors: Olan Stanley Fruchey, Bad Soden/T.S., Germany; Edward G. Zey; Larry O. Wheeler, both of Corpus Christi, Tex.

[73] Assignee: BASF Corporation, Mount Olive, N.J.

[21] Appl. No.: 08/213,375

[22] Filed: Mar. 15, 1994

Related U.S. Application Data

[63] Continuation of application No. 07/957,465, Oct. 6, 1992, abandoned, which is a continuation of application No. 07/608,106, Nov. 1, 1990, abandoned.

[51] Int. Cl.$^6$ .................................................. C07C 231/24
[52] U.S. Cl. ............................................ 564/216; 564/223
[58] Field of Search ....................................... 564/223, 216

[56] References Cited

U.S. PATENT DOCUMENTS

| | | | |
|---|---|---|---|
| 3,042,719 | 7/1962 | Hahn | 260/562 |
| 3,113,150 | 12/1963 | Young | 260/562 |
| 3,748,358 | 7/1973 | Baron | 260/562 P |
| 3,781,354 | 12/1973 | Kosak | 260/562 B |
| 4,524,217 | 6/1985 | Davenport et al. | 564/223 |

*Primary Examiner*—Shailendra Kumar
*Attorney, Agent, or Firm*—Barbara V. Maurer

[57] ABSTRACT

A method is provided for purifying a crude N-acetyl-para-aminophenol (APAP) containing color bodies or their precursors, the method comprising: a) forming a hot aqueous solution of the crude APAP; and b) subsequently contacting the hot solution with an acid washed adsorbent carbon, e.g., an activated carbon, which acid washed carbon, prior to such contact, has been pretreated by contacting it with an aqueous solution of a reducing sulfite.

8 Claims, No Drawings

METHOD FOR THE PURIFICATION OF ACETAMINOPHEN

This is a continuation of application Ser. No. 07/957,465 filed on Oct. 6, 1992, abandoned; which is a continuation of application Ser. No. 07/608,106 filed on Nov. 1, 1990, abandoned.

BACKGROUND OF THE INVENTION

1. Field of the Invention

This invention relates to an improved method for the purification of N-acetyl-para-aminophenol (APAP), also known as acetaminophen. APAP is a well-known over-the-counter analgesic and anti-pyretic agent.

2. Description of Related Art

The following prior art references are disclosed in accordance with the terms of 37 CFR 1.56, 1.97 and 1.98.

U.S. Pat. No. 3,042,719, issued Jul. 3, 1962 to Hahn et al., discloses the purification of crude discolored APAP by acidifying an aqueous solution of the APAP with a mineral acid, filtering the solution while hot, and cooling the filtrate while adding an alkaline reducing sulfite, e.g., sodium hydrosulfite (sodium dithionite). A "decolorizing" carbon may be added to the hot solution.

U.S. Pat. No. 3,113,150, issued Dec. 3, 1963 to Young, teaches the preparation of "pure" APAP by adding acetic anhydride to a mixture of p-aminophenol and water, cooling the reaction mixture to precipitate the APAP, filtering to remove excess acetic acid, neutralizing the wet APAP with ammonium hydroxide, and agitating the resulting solution with carbon black.

U.S. Pat. No. 3,748,358, issued Jul. 24, 1973 to Baron, discloses the purification of APAP by treating it in aqueous solution with carbon which has been preliminarily treated with an acidic solution.

U.S. Pat. No. 3,781,354, issued Dec. 25, 1973 to Kosak, teaches the purification of APAP by treating it in hot aqueous solution with ferric chloride and adsorbing the colored by-product on activated carbon.

U.S. Pat. No. 4,524,217, issued Jun. 18, 1985 to Davenport et al., teaches an integrated process for the production of APAP comprising acetylating phenol by a Friedel-Crafts reaction, or subjecting phenyl acetate to a Fries rearrangement to produce 4-hydroxyacetophenone (4-HAP), reacting the 4-HAP with hydroxylamine or a hydroxylamine salt to form 4-HAP oxime, and subjecting the latter oxime to a Beckmann rearrangement to form APAP.

3. Additional Background Information

In the manufacture of APAP by any of the known methods, it has been found that there is a tendency for color bodies and color body precursors to form which cause the crude product to have or to develop subsequently an undesirably colored appearance. Because of this, various methods have been developed for the purification of APAP, which remove color bodies in addition to other impurities, such that the purified product has a substantially pure white appearance. These methods often include the addition to a hot aqueous solution of APAP containing color bodies of an adsorbent carbon, which is a well-known decolorizing agent. Some of these methods are described in the disclosures of several of the previously cited references.

It has been found that a disadvantage of decolorizing APAP by contacting a hot aqueous solution of the crude APAP with an adsorbent carbon is that certain impurities appear for the first time or increase as a result of such treatment, which impurities were not present previously, i.e., in the crude APAP before purification. In view of the fact that the main use for APAP is as a pharmaceutical, the presence of these impurities must be kept to a very low practical maximum, either by preventing their formation, or removing the bulk of them subsequent to the carbon treatment.

SUMMARY OF THE INVENTION

In accordance with this invention, a crude APAP containing undesirable color bodies or their precursors is subjected to a purification treatment comprising the steps of forming a hot aqueous solution of the crude APAP, and subsequently contacting said hot solution with an acid washed adsorbent carbon which, prior to said contact, has been pretreated with an aqueous solution of a reducing sulfite. It has been found that the treatment of the acid washed carbon with the aqueous reducing sulfite solution substantially reduces the formation of certain impurities which are observed to form during the treatment of the hot APAP solution with carbon which has not been treated with the aqueous reducing sulfite solution. The impurities formed during the treatment of APAP with carbon which has not been sulfite treated are different from other impurities present in the crude APAP before carbon treatment, which other impurities do not increase as a result of the carbon treatment, as indicated by liquid chromatographic analysis.

DESCRIPTION OF PREFERRED EMBODIMENTS

The aqueous solution of APAP containing color bodies which is subjected to carbon treatment will in most cases contain at least about 4 wt. % of APAP and the solution will be at least hot enough to dissolve the APAP substantially completely, e.g., at least about 70° C. and up to the boiling point of the solution. The method of the invention is useful in the preparation of a relatively pure decolorized APAP regardless of the manufacturing process used to produce the APAP, since such method accomplishes the reduction of impurities, formed during treatment of the APAP with acid washed carbon which has not been pretreated with reducing sulfite, no matter which manufacturing process is used. Thus, the APAP may be produced, for example, by the process illustrated in the examples of previously cited U.S. Pat. No. 4,524,217 as summed up in the foregoing description of the disclosure of that patent, or by the previously developed process of acetylating para-aminophenol with acetic anhydride, as described, for example, in previously cited U.S. Pat. No. 3,113,150.

The acid washed adsorbent carbon of this invention defines an art-recognized group of materials and is a commodity of commerce. Such a carbon has a relatively large surface area available for the adsorption of impurities and is preferably one of the class of materials known as activated carbon or activated charcoal. The feature of the carbon being "acid washed" is well-known in the art and may be accomplished as described, for example, in previously cited U.S. Pat. No. 3,748,858.

The reducing sulfite used to pretreat the acid washed carbon may be any water soluble reducing sulfite such as alkali metal and ammonium reducing sulfites, e.g., sodium, potassium, and ammonium dithionites, metabisulfites, sulfites, and bisulfites. Preferably the sulfite reducing agent is a dithionite, and most preferably sodium dithionite. In pretreating the acid washed carbon with reducing sulfite, the carbon is shaken with a sufficient quantity of an aqueous solution of the sulfite containing, for example, about 0.1 to 5 wt. % of the sulfite, to completely wet the carbon. The carbon may then be allowed to stand in such wetted condition, e.g., submerged in the solution, for a period of at least ½ hour, preferably at least 1 hour. In some cases, it may be desirable to allow the wetted carbon to stand for at least 24 hours or longer.

After pretreatment with a reducing sulfite, the carbon is contacted with the hot aqueous APAP solution. The amount of carbon used is not critical but is generally such that the weight ratio of APAP to carbon (APAP:carbon) is at least about 2:1 and may be as high as about 200:1. The APAP solution is then agitated with the pretreated carbon, preferably under reflux, for a period of at least about 1 min. The solution is then filtered to remove the carbon and cooled to crystallize out the APAP. In some cases, it may be advantageous to conduct an initial crystallization of the APAP from hot aqueous solution without any carbon treatment, followed by a second crystallization from a hot aqueous solution which has been subjected to a carbon treatment using a reducing sulfite pretreated acid washed carbon in accordance with this invention. It may also be advantageous for the purpose of reducing the impurities to the lowest feasible level, to dissolve some reducing sulfite, e.g., from about 0.05 to about 0.5 wt. %, (based on the total solution mixture including the reducing sulfite) in the hot aqueous APAP solution which is subjected to carbon treatment. The latter reducing sulfite may be the same or different from the reducing sulfite used to pretreat the carbon, and is preferably sodium dithionite.

It is critical to this invention that the hot aqueous solution of the colored APAP be initially prepared and that the hot solution is then contacted with the pretreated acid washed carbon, rather than combining the APAP water and carbon at room temperature, and heating the entire composition to dissolve the APAP. In the latter procedure, the impurities which the inventive method is intended to minimize, are not formed during treatment with carbon which was not given a reducing sulfite pretreatment. While it is not desired to be limited by any theory of the invention, it may be postulated that the impurities which are formed during treatment with carbon which has not been given a sulfite pretreatment are oxidation products of the reaction between the APAP and the oxygen trapped in the pores of the carbon, which reaction can occur at the temperature of the hot solution. On the other hand, if the crude APAP, water and carbon are combined at room temperature and the composition is heated to dissolve the APAP, the carbon probably becomes deaerated during heating before the temperature is high enough for the oxidation reaction to occur. Despite this, it is much easier and more convenient in commercial operation to prepare the hot solution of crude APAP before the carbon treatment, with a concomitant formation of additional impurities which is minimized by the method of this invention as described.

The inventive method is designed to prevent or minimize the formation of primarily two impurities which form during conventional treatment of a hot solution of crude APAP with adsorbent carbon, which may be designated as impurity Y (unknown 18) and impurity Z (unknown 23). These impurities were not analyzed because of the extreme difficulty of extracting them from the carbon treated APAP and purifying them so as to have sufficient quantities of pure samples for detailed analysis. However, their presence and amounts in the carbon treated APAP are readily determined by conventional high performance liquid chromatography (HPLC) techniques, as more fully described hereinafter, and such amounts are believed to be undesirable in APAP used as a drug.

The invention is further illustrated by the following examples.

COMPARATIVE EXAMPLES A AND B

These examples illustrate the separate effects of an air sparge, and treatment with an acid washed adsorbent carbon which has not been pretreated with a reducing sulfite, on a hot aqueous solution of APAP.

A previously purified, pharmaceutical grade APAP sample was subjected to analysis by high performance liquid chromatography (HPLC), using a microbore reverse phase mode of separation and ultraviolet (UV) detection. The instrument utilized was a Hewlett-Packard LC equipped with a variable volume injection system and autosampler, the detector was a Hewlett-Packard filter photometric detector with wavelength set at 254 nm (filter no. 3), the column was a 10 cm×2.1 mm id Hewlett-Packard Hypersil ODS 5 micron column, the injection volume was 2 microliters, the eluents utilized at a flow rate of 0.2 mL/min. were methanol (A) and 0.5% acetic acid in water (B) which were HPLC grade and filtered through a 0.22 micron Teflon membrane before use. Linear gradient elution was used and the composition of the eluents utilized was 5 vol. % A and 95 vol. % B at up to 33 min. analysis time, 51 vol. % A and 49 vol. % B at 33 to 35 min., 90 vol. % A and 10 vol. % B at 35 to 42 min. and 5 vol. % A and 95 vol. % B at 42 to 44 min. The total analysis time was 44 min., including equilibration time, and the analysis was carried out at ambient temperature. The sample was prepared for analysis by dissolving 0.15 g in neat methanol and adding sufficient water to obtain a 5 wt. % solution of the sample in a 5/95 methanol/water solvent.

Using the foregoing apparatus and procedure, the sample was found to contain 23 ppm of impurity Y, which yielded a peak at 17.50 min. analysis (retention) time, after the peak for chlorinated APAP at 16.00 min. and before the peak for 4-hydroxyacetophenone at 17.77 min., and 19 ppm of impurity Z, which yielded a peak at 19.28 min., after the peak at 22.50 min. for 4-hydroxyacetophenone oxime.

In comparative Example A a 500 mL round bottom flask was charged with 50 g of the foregoing purified APAP and 375 mL of water. The contents were refluxed and air was sparged through the solution for 30 min. after which the solution was crash crystallized in an ice bath, filtered, washed with 50 mL of water and dried in a vacuum oven. Using the foregoing HPLC procedure the sample was found to contain 26 ppm of impurity Y and 28 ppm of impurity Z.

In Comparative Example B, the APAP feed was the product of Comparative Example A and the procedure of Comparative Example A was followed except that no air sparge was used. Instead, the contents of the flask were heated until the solids dissolved, 5 g of "ADP" carbon, an acid washed activated carbon manufactured by Calgon Corp., were added for a weight ratio of APAP/C of 10/1, and the solution was refluxed under an air atmosphere for 1 h, hot filtered through a celite pad to remove the carbon, and crystallized, filtered, washed and dried as described in Comparative Example A. The sample was then subjected to an HPLC analysis as previously described and found to contain 88 ppm of impurity Y and 203 ppm of impurity Z.

The results of Comparative Examples A and B indicate that an ordinary air sparge of an aqueous APAP solution does not cause the formation of impurities Y and Z in appreciable amounts, but that a treatment of the hot aqueous APAP solution with acid washed adsorbent carbon which has not been pretreated with a reducing sulfite does cause the formation of substantial amounts of these impurities.

Comparative Examples C and D illustrate the effect on the levels of impurities Y and Z of treating a hot aqueous solution of crude APAP with an acid washed adsorbent carbon which has not been pretreated with a reducing sulfite, at widely different APAP/C weight ratios, and Example 1 illustrates the effect of treating the same solution with an acid washed adsorbent carbon which was treated with reducing sulfite.

COMPARATIVE EXAMPLE C

A 250 mL round bottom flask was charged with 100 mL of water, and 10 g of crude APAP, prepared in accordance with the disclosure of U.S. Pat. No. 2,524,217 as described previously, and subjected to an initial crystallization without any carbon treatment. Such crude APAP contained 434 ppm of impurity Y and 19 ppm of impurity Z as determined by HPLC analysis. The contents were heated until the solids dissolved and 1 g of ADP carbon which had not been treated with a reducing sulfite, was added (weight ratio of APAP/C=10/1). Thereafter, the contents of the flask were refluxed under an air atmosphere, hot filtered through a celite pad to remove the carbon, crash crystallized in an ice bath, filtered, and the solids washed with 25 mL of water and dried in a vacuum oven. The sample was found by HPLC analysis to contain 538 ppm of impurity Y and 739 ppm of impurity Z.

COMPARATIVE EXAMPLE D

The procedure of Comparative Example C was followed except that 5 g of ADP carbon were used, for a APAP/C ratio of 2/1. HPLC analysis of the product indicated the presence of 466 ppm of impurity Y and 632 ppm of impurity Z.

EXAMPLE 1

The procedure of Comparative Example C was followed except that the 1 g of ADP carbon prior to use was pretreated by slurrying it with 25 mL of water containing 0.1 g of sodium dithionite and the slurry allowed to stand for 24 h. The APAP was found by HPLC analysis to contain 165 ppm of impurity Y and 17 ppm of impurity Z.

The results of Comparative Examples C and D indicate that treatment of a hot aqueous solution of APAP with acid washed adsorbent carbon at widely varying APAP/C ratios of 10/1 and 2/1 caused substantial increases of impurities Y and Z in the APAP. However, comparison of the results of Comparative Example C and Example 1 indicates that a pretreatment of the carbon with a reducing sulfite causes a substantial reduction in the content of these impurities.

COMPARATIVE EXAMPLES E AND F AND EXAMPLES 2 AND 3

These examples illustrate the effect of pretreating an acid washed adsorbent carbon with a reducing sulfite in minimizing the level of impurity Y in APAP, when the hot aqueous APAP solution being treated contains reducing sulfite dissolved therein.

The feed for these examples was a crude APAP prepared in accordance with the disclosure of U.S. Pat. No. 2,524,217, containing 24 ppm of impurity Y and previously subjected to a crystallization from a hot aqueous solution without carbon. In each example, a 1 liter round bottom flask was charged with 50 g of crude APAP, 0.2 g of sodium dithionite and 375 mL of water, the contents heated to dissolve the APAP, and 1 g of ADP carbon added to the flask. The carbon was either untreated (Comparative Examples E and F) or pretreated with a sodium dithionite solution as described in Example 1 (Examples 2 and 3). The solution was then either refluxed for 1 h under of nitrogen atmosphere (Comparative Example E and Example 2) or refluxed while air was bubbled through it for 1 h (Comparative Example F and Example 3). The contents of the flask were then hot filtered through a celite pad to remove the carbon and crash crystallized in an ice bath either under nitrogen (Comparative Example E and Example 2) or in air (Comparative Example F and Example 3). The solids in all the examples were then filtered, washed with 50 mL of ice water, and dried in a vacuum oven.

The conditions of these examples including whether the carbon was pretreated (C Pretr.), and the effect on the level of impurity Y (Imp. Y) determined by HPLC analysis, are shown in the table.

TABLE

| Example | Run No. | Air Sparge | C Pretr. | Imp. Y, ppm |
| --- | --- | --- | --- | --- |
| E | 2 | No | No | 29 |
| 2 | 3 | No | Yes | 23 |
| F | 1 | Yes | No | 30 |
| 3 | 4 | Yes | Yes | 23 |

The results of these examples indicate that even when a reducing sulfite is dissolved in the hot aqueous APAP solution, and whether or not an air sparge is used, the use of an acid washed adsorbent carbon which has not been pretreated with a reducing sulfite causes a rise in the level of impurity Y in the APAP while the same carbon which has been pretreated with reducing sulfite, does not cause such a rise.

We claim:

1. A method of purifying a crude N-acetyl-para-aminophenol (APAP) containing color bodies or their precursors comprising forming a hot aqueous solution of said crude APAP, and subsequently contacting said hot solution with an acid washed adsorbent carbon which prior to said contact has been treated by contacting it with an aqueous solution of a reducing sulfite.

2. The method of claim 1 wherein said carbon is an activated carbon.

3. The method of claim 1 wherein said reducing sulfite is sodium dithionite.

4. The method of claim 1 wherein said contact of carbon and reducing sulfite solution is carried out for at least ½ hour.

5. The method of claim 4 wherein said contact of carbon and reducing sulfite solution is carried out for at least 1 hour.

6. The method of claim 1 wherein said solution of reducing sulfite contains from about 0.1 to 5 wt. % of said reducing sulfite.

7. The method of claim 1 wherein said hot aqueous solution of crude APAP contains a reducing sulfite dissolved therein.

8. The process of claim 7 wherein said reducing sulfite dissolved in the hot aqueous solution of crude APAP is sodium dithionite.

* * * * *